United States Patent [19]

Davis et al.

[11] 4,031,885

[45] June 28, 1977

[54] METHOD AND APPARATUS FOR DETERMINING PATIENT LUNG PRESSURE, COMPLIANCE AND RESISTANCE

[75] Inventors: James E. P. Davis, Santa Monica; David M. Omelich, Cerritos, both of Calif.

[73] Assignee: Puritan-Bennett Corporation, Kansas City, Mo.

[22] Filed: Oct. 15, 1975

[21] Appl. No.: 622,536

[52] U.S. Cl. .............................................. 128/2.08
[51] Int. Cl.² ......................................... A61B 5/08
[58] Field of Search ........ 128/2.08, 145.8, DIG. 17

[56] References Cited

UNITED STATES PATENTS

| | | | |
|---|---|---|---|
| 3,509,767 | 5/1970 | Greer | 128/2.08 |
| 3,621,833 | 11/1971 | Crane | 128/2.08 |
| 3,818,901 | 6/1974 | Sanctuary et al. | 128/2.08 |
| 3,871,371 | 3/1975 | Weigl | 128/2.08 |
| 3,902,481 | 9/1975 | Bargeton et al. | 128/2.08 |
| 3,921,628 | 11/1975 | Smythe et al. | 128/DIG. 17 |
| 3,923,056 | 12/1975 | Bingmann et al. | 128/145.8 |

*Primary Examiner*—William E. Kamm

*Attorney, Agent, or Firm*—Fulwider, Patton, Rieber, Lee & Utecht

[57] ABSTRACT

A method and apparatus for determining patient lung pressure, compliance and resistance, for use in conjunction with a respirator system of the compensated-volume type wherein a predetermined volume of gas is delivered to the patient in each breathing cycle. The method and apparatus of the invention determine both the system pressure at the point of delivery to the patient and the patient lung pressure, both at the end of the inspiration phase of the breathing cycle, and utilize these values, together with a compensated volume signal, to compute the values of patient compliance and resistance. Control circuitry, actuated periodically or on demand, substitutes an enforced plateau period following inspiration, to allow the system pressure to fall to the value of lung pressure which is obtained at the end of the inspiration phase, thereby permitting the measurement of lung pressure by sampling system pressure at the end of the plateau period. The control circuitry also controls analog-to-digital converters which convert the computed values of pressure, compliance and resistance for display in a digital display device.

13 Claims, 8 Drawing Figures

METHOD AND APPARATUS FOR DETERMINING PATIENT LUNG PRESSURE, COMPLIANCE AND RESISTANCE

BACKGROUND OF THE INVENTION

This invention relates generally to the field of respiration apparatus, and related methods for its use, in which a predetermined volume of gas is delivered to a patient in each breath, as in the administration of intermittent positive pressure breathing therapy. More particularly, the invention relates to a method and apparatus for the determination of the patient-dependent parameters of lung pressure, compliance and resistance, so that these parameters can be continuously displayed to the operator of the respiration apparatus.

Respiration apparatus used in administering intermittent positive pressure breathing therapy is well known in the art. In this type of therapy, a predetermined volume of air, or other breathable gas mixture, is delivered to the patient during an inspiration phase of the breathing cycle, and, during an expiration phase, the patient exhales against a pressure which may or may not be equal to atmospheric pressure, depending upon the exact nature of the therapy being provided. Since the predetermined volume is usually measured by means of a cylinder within the apparatus, and since part of this volume inevitably does not reach the patient but is retained in delivery tubes within the apparatus, it is well known that the volume actually reaching the patient, known as the tidal volume, will not always be the same as the volume measured by the cylinder in the apparatus. Moreover, the actual volume delivered will depend on the delivery pressure and various other factors. Consequently, some respirator systems include means for compensating for these errors in delivered volume, and for providing the desired volume, referred to as the compensated volume, to the patient, regardless of variations in delivery pressure. Such apparatus may be referred to as volume-compensated respiration apparatus. The present invention is principally concerned with the determination of a patient's lung pressure, compliance and resistance in conjunction with the administration of breathing therapy using volume-compensated respiration apparatus.

The patient resistance is a measure of the resistance to the flow of gas between the point of delivery of the gas to the patient, usually the mouth, and the patient's lungs. The measure of resistance is the pressure drop between the mouth and lungs divided by the volume rate of flow to the lungs, and the units of resistance are usually centimeters of water per liter per second. A high patient resistance may be indicative of a large blockage in the patient's mouth or trachea, and an increase in resistance may, for example, be indicative of a build up of mucus somewhere between the mouth and lungs.

The compliance of a patient's lungs is a measure of their resilience. The units of compliance are volume divided by pressure. Thus, a relatively compliant lung will expand to a large volume at a given pressure, while a lung of low compliance will be relatively stiff and unyielding as pressure is increased. Generally, an increase in patient lung compliance is indicative of an improvement of the patient's condition, but, in any event, the continued availability of both compliance and resistance information, and of lung pressure, is an extremely valuable tool to doctors or therapists treating patients under respiratory care.

The determination of patient compliance and patient resistance requires the measurement of the tidal volume. In volume-compensated systems, the tidal volume should be equal to the compensated volume, the value of which is known in such systems. The determination of compliance and resistance also requires the measurement of the patient lung pressure, as distinguished from system pressure at the point of delivery to the patient. Short of placing a pressure transducer in the lung, the accurate measurement of lung pressure has not been possible with available systems. Accordingly, respirator systems available heretofore have not provided for the accurate determination of patient resistance and compliance. It will be appreciated from the foregoing that a need exists for such a system. The present invention fulfills this need.

SUMMARY OF THE INVENTION

The present invention resides in a method and apparatus for the determination of patient lung pressure, compliance and resistance for use in conjunction with respirator apparatus of the volume-compensated type. Briefly, and in general terms, the apparatus of the invention includes means for determining lung pressure at the end of the inspiration phase of the breathing cycle, by sampling the system pressure some predetermined time after the end of inspiration but before expiration is allowed to begin, by which time system pressure is substantially equal to lung pressure at the end of the inspiration phase. The apparatus further includes means for determining the respirator system pressure at the end of the inspiration phase, and means for computing patient compliance and resistance from the lung and system pressures at the end of the inspiration phase, and from other parameters available in the volume-compensated respiration apparatus.

The breathing cycle of a patient undergoing intermittent positive pressure breathing therapy sometimes includes, in addition to the inspiration and expiration phases, a brief interval known as a plateau immediately following the end of inspiration. During the plateau, no more breathing gas is supplied to the patient for inspiration, but the expiration valve of the apparatus is held closed, thus preventing expiration for a short time. As soon as the expiration valve is opened, the expiration phase begins, and this is followed immediately by the next inspiration phase. During the plateau period, the respiration system supply pressure falls rapidly, and since there is no flow from the system to the patient's lungs, the system supply pressure rapidly equilibrates with the static pressure which was present in the lungs when inspiration ended. Thus, if the supply system pressure is measured right at the end of the inspiration phase and again at the end of the plateau, a measure is obtained of both the system supply pressure and of the lung pressure at the end of the inspiration phase.

Accordingly, the novel method of the present invention includes, in general terms, the steps of monitoring the system pressure during each breathing cycle, sampling the system pressure at the end of the plateau, and thereby determining the lung pressure. Additionally, the method includes sampling the system pressure at the end of the inspiration phase, and computing the patient compliance and resistance from the sampled pressure values.

Since the respiration system is a volume-compensated one, a measure of the tidal or compensated volume is also readily available, and the patient compliance can be determined by dividing the compensated volume by the static pressure in the lungs at the end of inspiration. Similarly, the patient resistance can be obtained by dividing the pressure drop between the supply system and the lungs at the end of the inspiration phase by the time differential of the compensated volume.

In a presently preferred embodiment of the invention, these computations are performed using electrical analog devices, and the invention further includes analog-to-digital conversion means, and digital display means for displaying the patient compliance and resistance at or near the respiration apparatus. It will be appreciated, however, that the computations could equally well be performed by digital logic.

Typically, respiration systems of the type described will include some form of control over the plateau period in the breathing cycle. In accordance with a further aspect of the invention, the invention apparatus includes control circuitry for temporarily disabling this plateau timing control and substituting a fixxed preselected plateau time for the measurement of the patient compliance and resistance. The control circuitry may be actuated either manually, to initiate computation and display of compliance and resistance in the next-occurring breathing cycle, or automatically on a periodic basis. Whether the control circuitry is initiated manually or automatically, its effect is to substitute a fixed plateau time in the next breathing cycle, and to initiate conversion and display of the compliance and resistance values at the end of that breathing cycle.

It will be appreciated from the foregoing that the present invention represents a significant advance in the field. As already pointed out, the availability of a display of the values of patient lung pressure, compliance and resistance is of much importance in the administration of breathing therapy. Other aspects and advantages of the invention will become apparent from the following more detailed description taken in conjunction with the accompanying drawings.

DESCRIPTION OF THE PREFERRED EMBODIMENT

As shown in the drawings for purposes of illustration, the present invention resides in a system for the determination of the lung pressure, compliance and resistance of a patient undergoing respiration therapy. As is well known in the art, compliance and resistance are important patient-dependent parameters, the knowledge of which is extremely useful to doctors or therapists administering respiration therapy. Patient compliance is akin to a measure of the resilience of the patient's lung or lungs, and is defined as lung volume divided by lung pressure; and patient resistance is the frictional resistance to the flow of air between the point at which it is delivered to the patient and the patient's lungs.

In mathematical terms, compliance and resistance are given by the equations:

$$C = V_c/P_s, \text{ and } R = P_D - P_S/V_C$$

where
C = compliance,
R = resistance,
$P_D$ = system pressure at end of the inspiration phase,
$P_S$ = lung pressure at end of the inspiration phase,
$V_C$ = compensated volume delivered during the inspiration phase, and
$\dot{V}_C$ = the time differential of $V_C$ at end of the inspiration phase.

The physical significance of compliance and resistance can perhaps be better appreciated by noting that there is an accurate electrical analogy to the parameters of patient compliance and resistance. The patient compliance is analogous to electrical capacitance, and the patient resistance is analogous to electrical resistance. During inspiration, the filling of the patient's lungs is analogous to the charging of an electrical capacitance through an electrical resistance, and during expiration the analogy is to the discharge of the capacitance through the same resistance.

Figure 1:
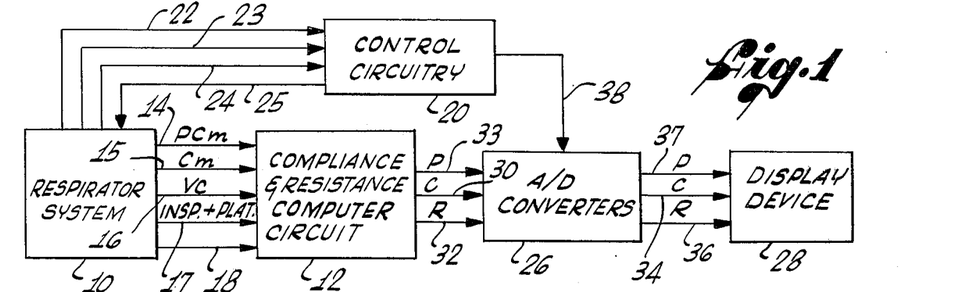
FIG. 1 is a simplified block diagram showing how the present invention is utilized in conjunction with a respirator system of the volume-compensated type.

As FIG. 1 shows, the apparatus of the invention is connected to a typical respirator system 10, and includes, in basic terms, a compliance and resistance computer circuit 12, connected with the respirator system by lines 14–18 for monitoring various analog and digital signals relating to the operation of the respirator system. The apparatus further includes control circuitry 20, also communicating with the respirator system, over lines 22–25, analog-to-digital converters 26, and a display device 28 for displaying the resultant values of pressure, compliance and resistance.

In general terms, the function of the compliance and resistance computer circuit 12 is to compute patient compliance and resistance from values of pressure and volume, and from logical signals relating to the various timing phases of the patient's breathing cycle, all received on lines 14–18. The compliance and resistance are transmitted to the analog-to-digital converters 26 over lines 30 and 32, and the lung pressure may also be transmitted to the converters, as shown by line 33. The analog values of compliance, resistance and pressure are converted to digital form and transmitted, in turn, over lines 34, 36 and 37, respectively, to the display device 28, which may, for example, take the form of an illuminated display, or a printing device. The control circuitry 20, as will be seen, may be initiated either manually or automatically to activate the analog-to-digital converters 26 at an appropriate time, as indicated by line 38, and to take over certain timing controls from the respirator system 10 during the particular breathing cycle in which the pressure, compliance and resistance are to be computed. The pressure, compliance and resistance are not computed during every breathing cycle, but only either on demand or periodically, at the option of the operator.

For purposes of explanation, a typical respirator system, in conjunction with which the invention can be used, will be briefly described. Such a system is illustrated in simplified form in FIG. 2. Basically, the system includes an oxygen or compressed air supply 40, and a volume generator 42 which typically includes a cylinder 44 and a piston assembly 46. The oxygen is supplied over line 48 to the upper side of the piston assembly 46, through appropriate valving which has been omitted from the drawing for simplicity. During the inspiration phase of the patient's breathing cycle, air is supplied to the lower side of the piston assembly 46 from an air supply 50, through an inspiration valve 52, a flow control valve 54, and line 56, and the piston assembly is raised through the appropriate distance to deliver a preselected volume of gas into line 58 to the patient, indicated at 60. An expiration valve 61 is opened after the patient has finished inhaling, to allow exhalation, usually to the atmosphere.

Figure 2:
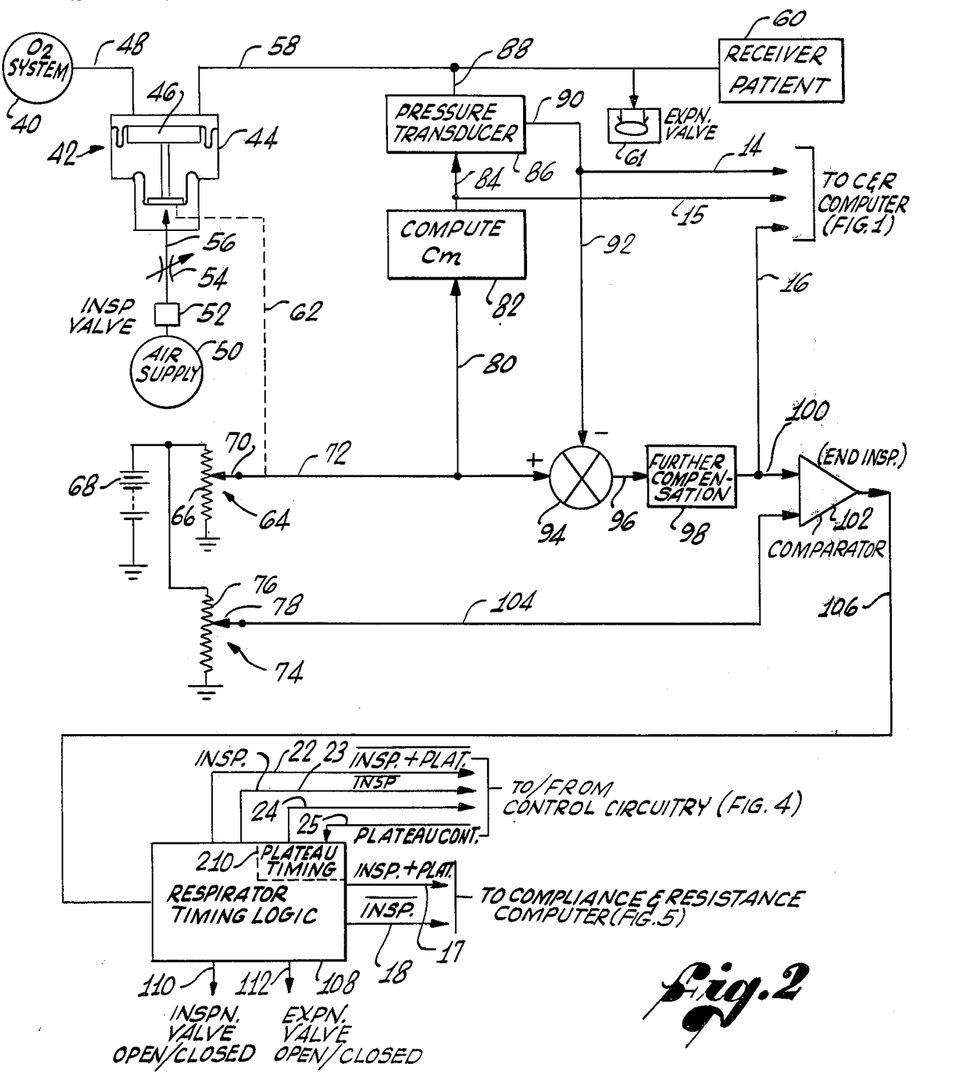
FIG. 2 is a simplified block diagram of a typical volume-compensated respirator system, showing the sources of the various analog and logical signals utilized in the apparatus of the invention.

In volume-limited respiration systems, in which a preselected volume of gas is delivered to the patient, some means must be provided for developing a signal indicative of the condition that the preselected volume has been delivered to the patient. At that point, the inspiration valve 52 can be closed, prior to the start of expiration. It is well understood in the respirator art that measuring the volume delivered by the volume generator 42 is subject to a number of significant errors, the principal one being that some portion of this volume is not, in fact, delivered to the patient at all, but is taken up in portions of the system itself, such as the delivery line 58. This latter error is usually referred to as being due to the compliance volume of the system. The error cannot be corrected by a constant correction applied to the piston assembly 46, because the error will be dependent on the system pressure, and system pressure may vary from one patient to another.

Consequently, in some respirator systems there are means to compensate for the error due to system compliance volume, using a pressure-dependent correction. One such means in simplied form is illustrated in FIG. 2, and is significant to the present invention only in that the compensated or tidal volume, i.e., the volume actually delivered to the patient, is needed in the present invention in order to compute both compliance and resistance.

As indicated diagrammatically by the broken line 62, the position of the piston assembly 46, and hence the volume delivered from the cylinder 44, is determined by means of a potentiometer 64, consisting of a resistor 66 across which a voltage source 68 is connected, and a sliding contact 70 which is mechanically connected to the axial movement of the piston assembly 62. Thus, the signal on line 72 from the sliding contact 70 is indicative of the volume delivered from the cylinder 44. A second potentiometer 74, also consisting of a resistance 76 and a sliding contact 78, is connected to the same voltage source 68, and is manually adjustable to provide an indication of the preselected volume of gas desired to be delivered to the patient.

The measured volume signal on line 72 is also transmitted over line 80 to circuitry 82 which computes the compliance of the respirator system, referred to by the symbol $C_m$. The system compliance computation will depend on the exact nature of the respiration system, but typically $C_m$ will be a function of the system volume. The system compliance is made available to the compliance and resistance computer circuitry 12 (FIG. 1) on line 15, and is also connected, by line 84, to drive a pressure transducer circuit 86, the latter including a pressure transducer located in the delivery line 58 to the patient, as indicated by the line 88. The pressure transducer circuit 86 generates a signal on line 90 proportional to the product of the system pressure at the point of delivery to the patient and the system compliance $C_m$. The product is, in effect, a measure of the system compliance volume, and this quantity is also made available to the compliance and resistance computer 12 (FIG. 1) on line 14.

The system compliance volume, on line 92, is subtracted from the measured volume on line 72 in a subtracting junction, indicated at 94. The resultant signal, on line 96, is indicative of a measured volume compensated for errors due to the system compliance. This signal may be further compensated, in the circuit shown at 98, for various other sources of error in the measurement of tidal volume, and a resultant compensated volume is applied over line 100 to a comparator 102, and also transmitted to the compliance and resistance computer circuit 12 (FIG. 1) over line 16. The other input to the comparator 102 is the preselected volume, on line 104 from potentiometer 74, and the output from the comparator on line 106 is a digital signal indicating the end of the inspiration phase of the breathing cycle.

The respirator system as illustrated in FIG. 2 also has timing logic 108 to which the end-of-inspiration signal on line 106 is connected, and from which are obtained logic signals for the control of the inspiration valve 52 and the expiration valve 61 on lines 110 and 112, respectively. Other timing signals are also derived from the timing logic 108 on lines 17, 18 and 22-25, and the purpose of these will become apparent from the discussion which follows.

Figure 3:
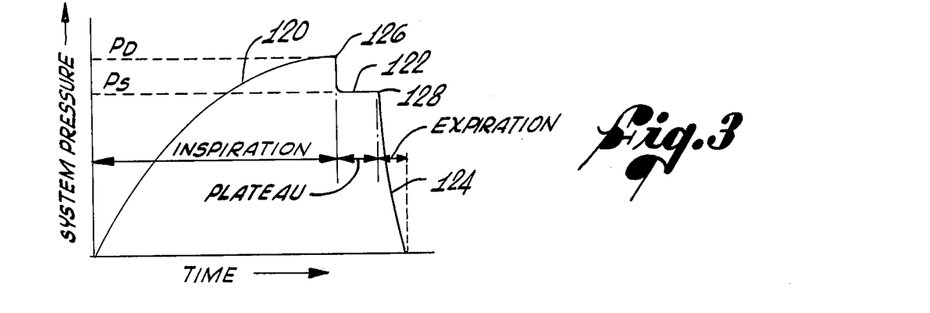
FIG. 3 is a pressure-versus-time graph illustrating a typical breathing cycle in the administration of intermittent positive pressure breathing therapy.

As shown in FIG. 3, a typical patient breathing cycle comprises an inspiration phase, during which a preselected volume of a breathable gas mixture is inspired by the patient, a plateau, and an expiration phase. During the inspiration phase, the expiration valve 61 (FIG. 2) is, of course, closed, and the inspiration valve 52 (FIG. 2) is open to provide delivery of a preselected volume of air or other gas mixture. During this inspiration phase, the system pressure rises as shown by the curve 120. The lung pressure also rises steadily during the inspiration phase, but, because of a pressure drop across the patient resistance, the lung pressure will be significantly lower than the system pressure during this phase.

At the end of inspiration, the inspiration valve 52 (FIG. 2) is closed, but the expiration valve 61 (FIG. 2) also remains closed for the plateau period, which may be selected as any desired interval, usually between 0 and about 2 seconds. During the plateau, indicated at 122, since the system is a closed one and there is no further flow to the lungs, the system pressure and lung pressure equalize after a short period of time. Thus, the system pressure falls rapidly at the start of the plateau period, and, after a brief interval of time, the system pressure attains a value approximately equal to that of the lung pressure at the end of the inspiration phase. At the end of the plateau period, the expiration valve is opened, and, as shown at 124 the system pressure falls rapidly as the patient exhales.

It can be seen from the pressure curve of FIG. 3 that an enforced plateau during the patient breathing cycle provides a convenient means for determining the lung pressure at the end of the inspiration phase. Since the respiration system may, by operator choice, be operated with a relatively short plateau, an enforced plateau of substantial length is needed to ensure an accurate measurement of lung pressure, and a resultant accurate measure of patient compliance and resistance. In brief, the detailed apparatus now to be described derives a measure of system pressure and lung pressure at the end of the inspiration phase, by measuring system pressure at the end of the inspiration phase (i.e., at 126 in FIG. 3) and at the end of the plateau period (i.e., at 128 in FIG. 3). From these pressures, and from a measure of the compensated or tidal volume delivered to the patient, values of patient compliance and resistance are computed and displayed.

Figure 5:
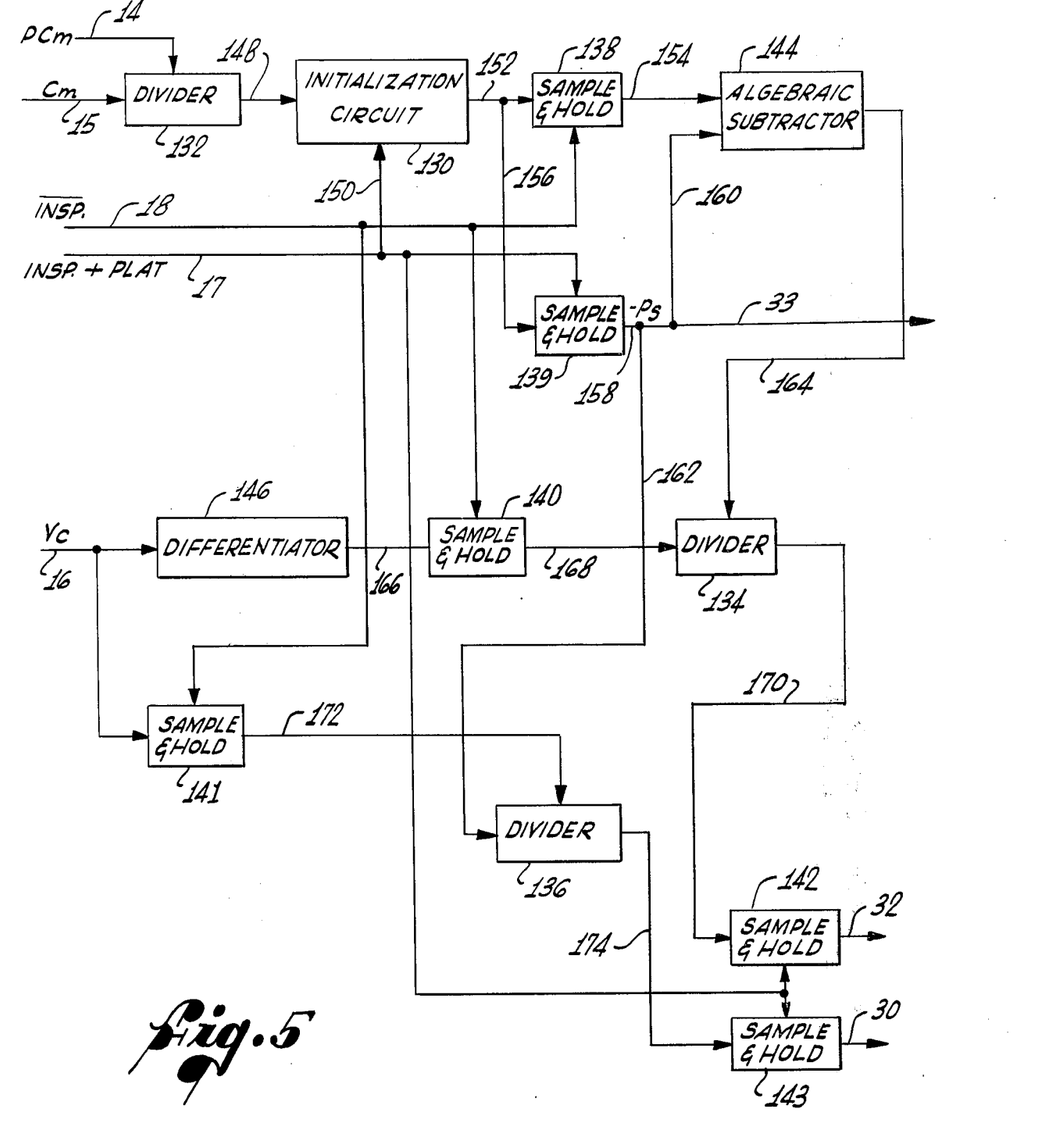
FIG. 5 is a block diagram of that portion of the apparatus of the invention which computes patient compliance and resistance from the signals obtained from the volume-compensated respiration system.

The basic functions performed by the compliance and resistance computer circuit 12 (FIG. 1) can best be understood by reference to FIG. 5, which is a block diagram showing the logical and arithmetic functions performed by the circuit 12. As shown in FIG. 5, the compliance and resistance computer circuit 12 (FIG. 1) includes an initialization circuit 130, the function of which will be explained in more detail, three divider circuits 132, 134 and 136, six sample-and-hold circuits 138–143, an algebraic subtracting circuit 144, and a differentiator circuit 146. Signals representative of the product of pressure and system compliance, on line 14, and of system compliance alone, on line 15, are input to the divider 132, so that the output is a pure pressure signal on line 148, connected to the initialization circuit 130.

The purpose of the initialization circuit 130 is to insure that the electrical voltage indicative of pressure at the start of the inspiration phase is zero. The logical signal on line 17 indicates whether the breathing cycle is in the inspiration or plateau phases, i.e., the signal becomes a logical "one" at the start of inspiration and remains in that condition until end of plateau. The initialization circuit 130 utilizes this logical signal, as indicated by line 150, to offset the pressure signal on line 148 starting at the beginning of inspiration. Thus, the pressure on line 152 from the initialization circuit to the sample-and-hold circuit 138 is a pressure signal referenced to a zero signal at the start of the inspiration phase. The sample-and-hold circuit 138 is triggered by a signal on line 18 indicative of whether the breathing cycle is in the inspiration phase or not. Thus, at the end of the inspiration phase, when the signal on line 18 changes state, the sample-and-hold circuit 138 will produce a signal on line 154 indicative of the system pressure at the end of the inspiration phase, i.e., the pressure at 126 in FIG. 3. The pressure signal on line 152 is also connected by line 156 to sample-and-hold circuit 139, which is gated by the logic signal on line 17 indicative of the states of inspiration or plateau. Thus, at the end of plateau, sample-and-hold circuit 139 is gated, to generate at its output on line 158, and on line 33 to the analog-to-digital converters 26 (FIG. 1), a signal proportional to the lung pressure at the end of the inspiration phase, i.e., the pressure measured at 128 in FIG. 3.

The lung pressure signal from the sample-and-hold circuit 139 is also connected by line 160 as an input to the algebraic subtractor 144, and by line 162 to the divider 136. Thus, the output of the algebraic subtractor 144, on line 164, is representative of the difference between system pressure and lung pressure at the end of the inspiration phase. A signal indicative of the compensated volume delivered to the patient is input to the differentiator 146 on line 16. Thus the output from the differentiator 146 is proportional to the time differential of the compensated volume signal. This time-differentiated signal is input over line 166 to sample-and-hold circuit 140, which is gated by the logical inspiration signal from line 18. Thus, the output of the sample-and-hold circuit 140 on line 168 to divider 134 is indicative of the time differential of the compensated volume signal as measured at the end of the inspiration phase. It can be seen, then, that divider 134 has as inputs the pressure difference signal from the algebraic subtractor 144 and the time differential of the volume signal on line 168. Consequently, the output of divider 134 on line 170 is the pressure difference signal divided by the differential of the compensated volume signal, which, as has been shown, is the mathematical expression for the patient resistance. Thus, the patient resistance value is output from divider 134 on line 170, is sampled and held in the sample-and-hold circuit 142, and is available to the analog-to-digital converters 26 (FIG. 1) on line 32.

The compensated volume signal on line 16 is also input to the sample-and-hold circuit 141, which is gated by the inspiration signal on line 18. The output of sample-and-hold circuit 141, which is therefore indicative of the compensated volume at the end of the inspiration phase, is connected by line 172 to divider 136, the other input of which is obtained from the lung pressure signal over line 162. The output of divider 136 on line 174 is therefore proportional to the compensated volume divided by the lung pressure, which, as has been seen, is the expression for the patient compliance. The final sample-and-hold circuit 143, also gated by the inspiration-or-plateau signal on line 17, holds the compliance value for output on line 30 to the analog-to-digital converters 26 (FIG. 1).

The detailed implementation of the compliance and resistance computer circuit which has been described with reference to the block diagram of FIG. 5, can, of course, take a variety of forms. The detailed circuitry used in a presently preferred embodiment of the invention is shown by way of example in FIGS. 6a and 6b. The part numbers given in FIGS. 6a and 6b, and in FIG. 7, which shows the control circuitry in detail, are standard throughout the industry, except for the following designations which are used by specific manufacturers: The divide circuits 132, 134 and 136 designated AD532KD are manufactured by Analog Devices, Norwood, Mass.; the operational amplifiers designated 8043C are manufactured by Intersil, Inc., Cupertino, Calif.; and the field effect transistors designated U305 are manufactured by Siliconix, Inc., Santa Clara, Calif. It is not believed to be necessary to discuss the specific design of FIGS. 6a and 6b in detail, except with regard to the initialization circuit 130 described generally with reference to FIG. 5.

Figure 6A:
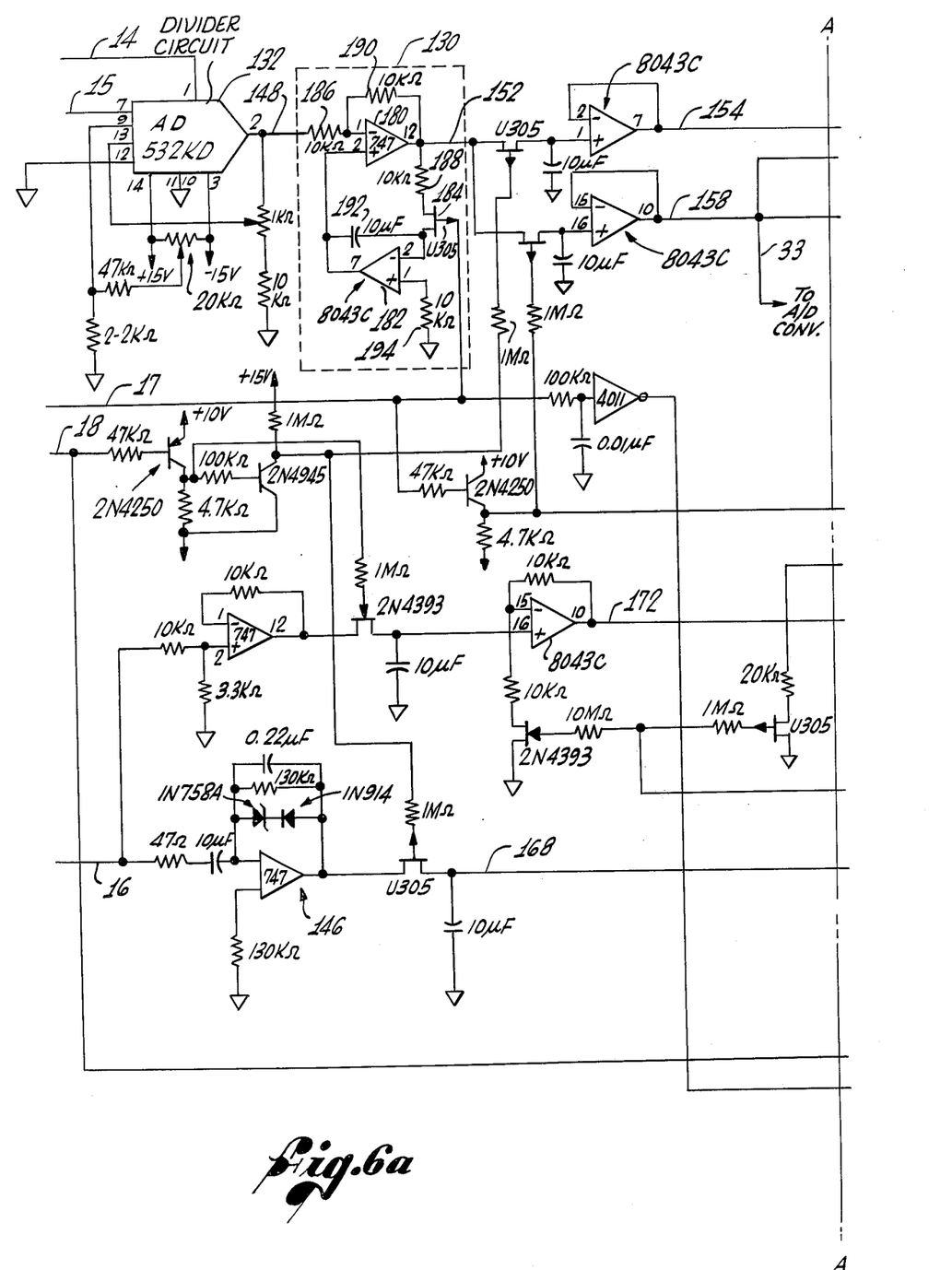
FIGS. 6a and 6b together comprise a schematic diagram of the apparatus of the invention, corresponding substantially to the block diagram of FIG. 5.
Figure 6B:
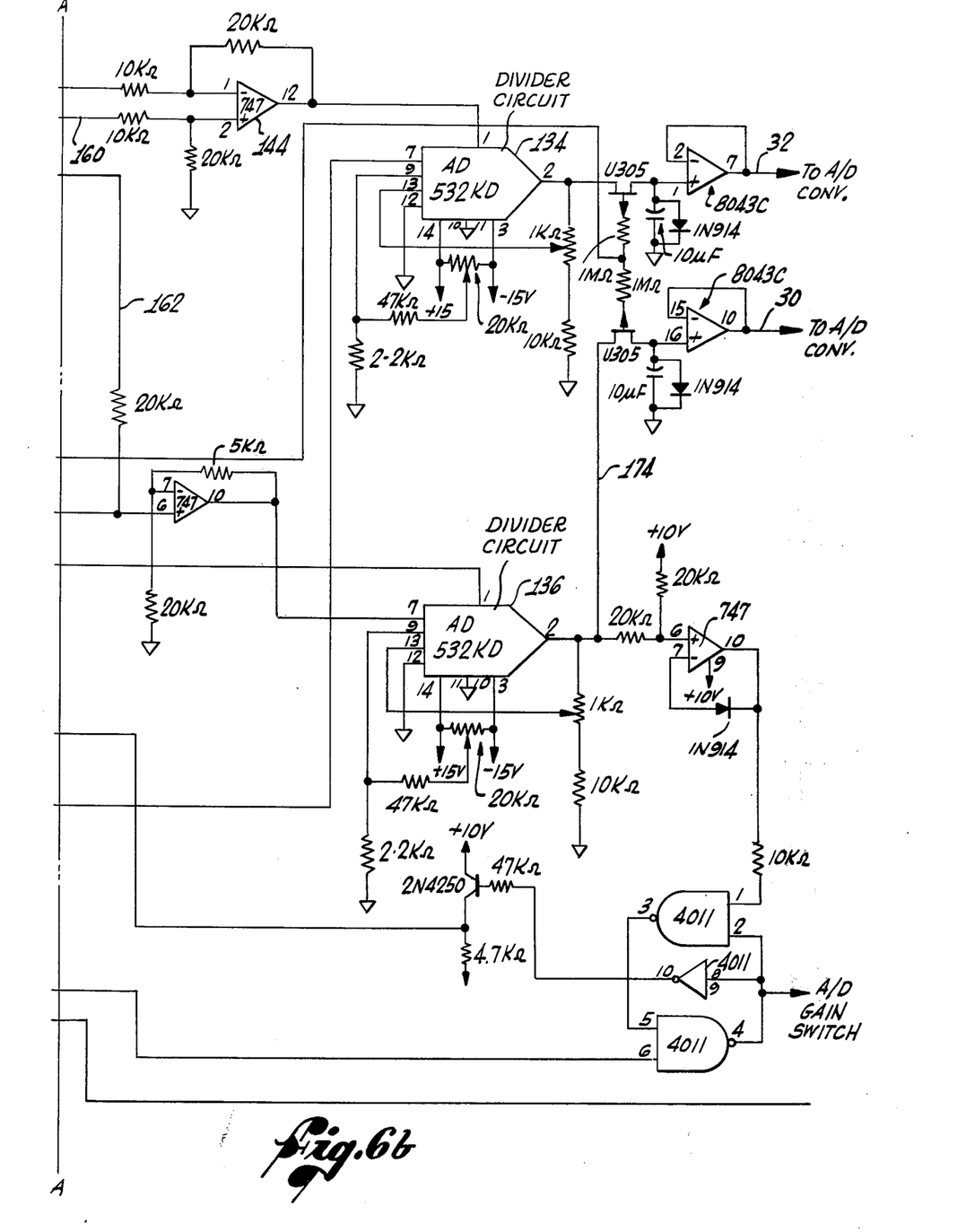

As can be seen in FIG. 6a the initialization circuit 130 includes two operational amplifiers 180 and 182, and a field effect transistor 184. The pressure signal on line 148 is connected through a resistor 186 to the negative terminal of operational amplifier 180, the output of which, on line 152 is connected through a resistor 188 and the field effect transistor 184 to the negative input of the other operational amplifier 182. The output of operational amplifier 182 is connected back to the positive input of operational amplifier 180. There is a feedback resistor 190 from the output of the first operational amplifier 180 to its negative input, and a feedback capacitor 192 from the output of the second operational amplifier 182 to its negative input. The positive input of the second operational amplifier is grounded through a resistor 194. The gate terminal of the field effect transistor 184 is connected to the inspiration-or-plateau signal on line 17, so that the transistor is in a conductive state only when the breathing cycle is not in the inspiration or plateau phases, i.e., when it is in the expiration phase.

When the field effect transistor 184 is conducting, the operational amplifier 182 operates as an integrator circuit, and it generates a voltage at the input of the first operational amplifier 180 which is proportional to the negative of the time integral of its output. It can be seen that, during the expiration phase, the output of the first operational amplifier 180 will quickly become zero and remain at zero regardless of the input on the negative input terminal. When the field effect transistor 184 is rendered non-conducting at the beginning of the inspiration phase, the integrator circuit will be effectively disconnected, but there will be sufficient residual charge on the capacitor 192 to apply an appropriate offset voltage to the positive terminal of the first operational amplifier 180, and to thereby ensure that the pressure signal at the output terminal on line 152 is accurately referenced to a zero voltage at the beginning of the inspiration phase.

Figure 4:
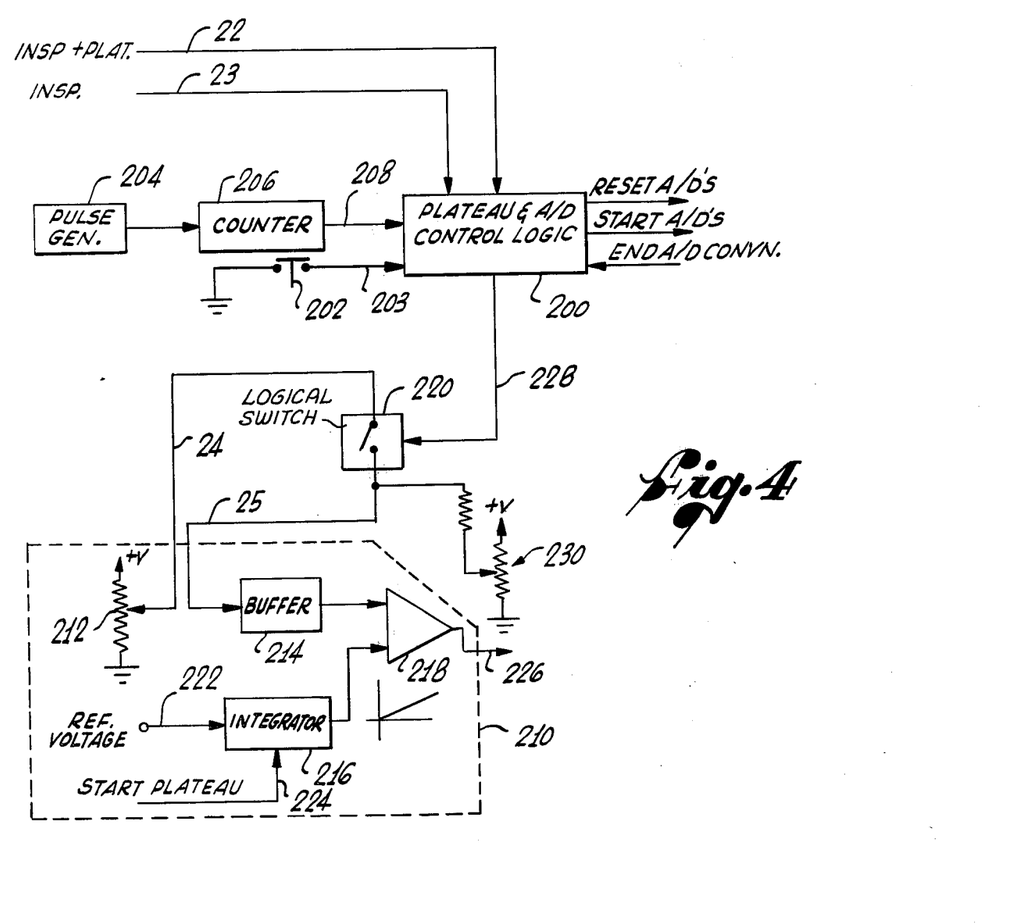
FIG. 4 is a simplified block diagram of control circuitry included in the present invention, together with portions of a typical plateau timing control circuit.

The control circuitry 20 (FIG. 1) needed to control the analog-to-digital converter 26 (FIG. 1) will now be described in more detail with reference to FIGS. 4 and 7. As shown in FIG. 4, the control circuitry includes plateau and analog-to-digital control logic, indicated at 200, and receives logical signals indicative of inspiration-or-plateau, and inspiration, over lines 22 and 23, respectively. The control logic 200 may be initiated by either of two techniques. Either a switch 202 may be grounded to provide a starting signal on line 203 to initiate computation and display of patient compliance and resistance, or the logic may operate periodically and automatically under control of a pulse generator 204 and counter 206, arranged to generate a starting signal over line 208 to the control logic 200.

One major function of the control circuitry is to substitute an enforced plateau period for the plateau period selected by the operator of the respirator apparatus. The respirator timing logic 108 (FIG. 2) includes plateau timing logic 210, illustrated within the broken lines in FIG. 4. This plateau timing logic 210 includes a voltage divider 212, a buffer 214, an integrator 216 and a comparator 218. When the operator-selected plateau time is being utilized by the apparatus a signal from the voltage divider 212 is transmitted, over lines 24 and 25, through a logical switch 220 in the control circuitry, the latter being closed to permit passage of this signal. A voltage indicative of the selected plateau time is held in the buffer 214, and is input to one terminal of the comparator 218. The other terminal of the comparator 218 is connected from the output of the integrator circuit 216, which receives as inputs a reference voltage on line 222 and a signal on line 224 indicating start of the plateau period. The integrator output is a ramp voltage starting at zero at the beginning of the plateau period, and this ramp voltage is therefore compared in the comparator 218 with the voltage held in the buffer 214. When equality is detected by the comparator 218, an output is generated on line 226, indicative of the end of the plateau period.

When the computation and display of patient compliance and resistance has been initiated, either by closing of the switch 202 or by means of the pulse generator 204 and counter 206, a signal is generated on line 228 to the logical switch 220, opening the same. A substitute voltage divider circuit 230 is thereby placed in the circuit, and a voltage signal indicative of a substitute plateau period is conveyed to the buffer 214 for comparison with the integrator ramp voltage in the comparator 218. This periodically or manually initiated substitution of an enforced plateau period apparently has little or no adverse effect on the patient undergoing therapy, but ensures equalization of system and lung pressures during the plateau period, and thereby allows accurate computation and display of the required patient parameters of compliance and resistance.

Figure 7:
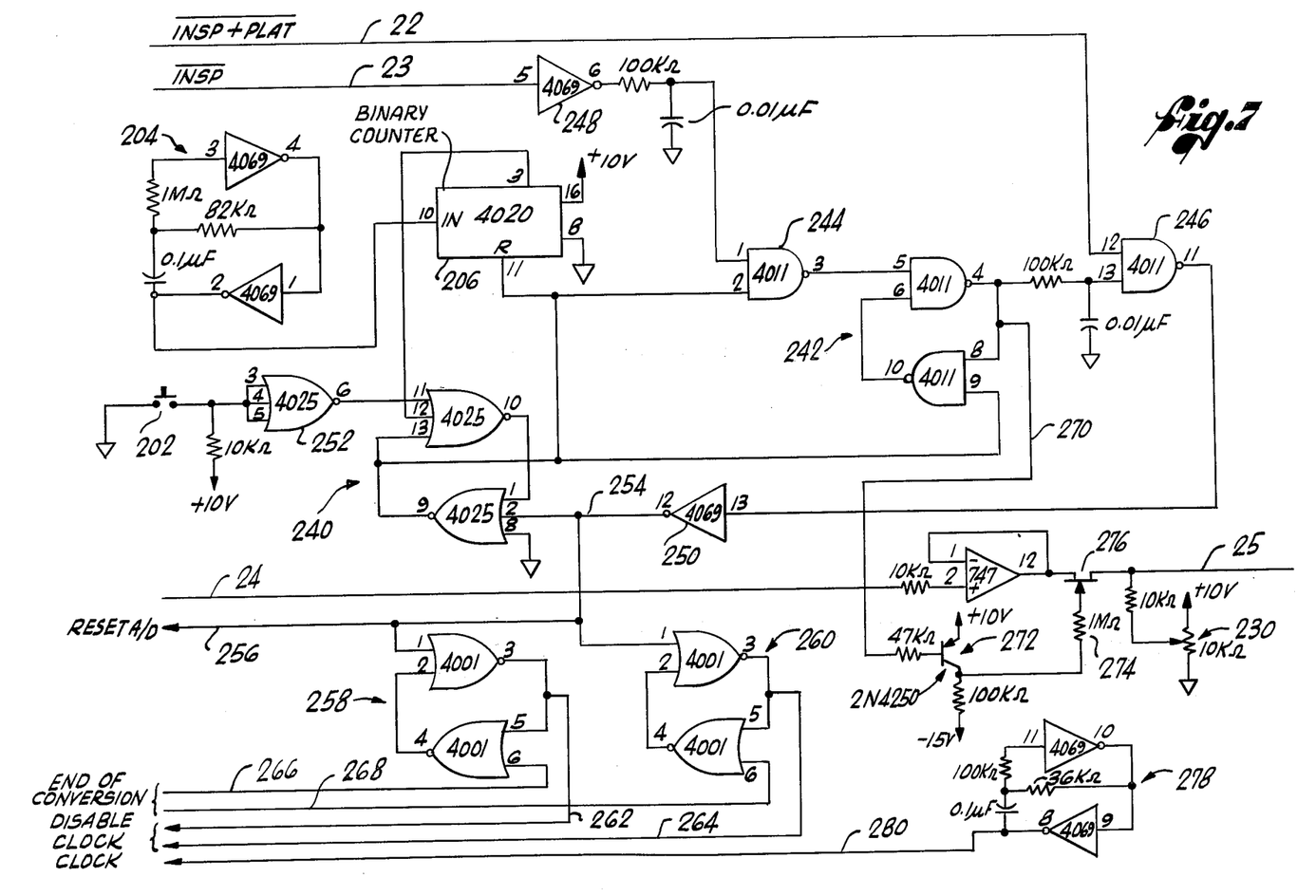
FIG. 7 is a schematic diagram of the control circuitry of the invention corresponding to the block diagram of FIG. 4.

FIG. 7 shows the control circuitry 20 (FIG. 1) in detail. Again, these design details are not believed to be critical to the invention, and any logical design for performing the functions to be described could be employed.

The pulse generator 204 is an astable multivibrator generating square-wave pulses at approximately 44 hertz, and the counter 206 is a conventional 14-stage binary counter. As illustrated, logical signals indicative of inspiration-or-plateau, and inspiration, respectively, are input on lines 22 and 23. The control logic includes a first flip-flop 240 consisting of two NOR gates, a second flip-flop 242 consisting of two NAND gates, two further NAND gates 244 and 246, two inverters 248 and 250, and another NOR gate 252 used as an inverter. Knowledge of the detailed operation of this logic is not believed to be necessary to an understanding of the invention. It can be readily verified from elementary analysis of FIG. 7 that, at the end of the plateau period immediately following initiation of the control circuitry, either manually by closure of the switch 202, or automatically, using the pulse generator 204 and counter 206, a logical "one" is generated on output line 254 from inverter 250. This logic level is utilized to reset both analog-to-digital converters by means of a reset signal on line 256, and to set two further flip-flop 258 and 260, respectively. When these flip-flops 258 and 260 are in the reset condition they have high or "one" outputs on lines 262 and 265, to disable analog-to-digital clock signals at the two analog-to-digital converters 26 (FIG. 1). When the logical "one" signal on line 254 occurs, the flip-flops 258 and 260 are set, and the signals on lines 262 and 264 drop to a zero level, thus enabling the clock signals and allowing analog-to-digital conversion of the compliance and resistance values. At the completion of conversion, signals on lines 266 and 268 from the analog-to-digital converters 26 (FIG. 1) reset flip-flops 258 and 260 again. It will be appreciated that an additional flip-flop (not shown) similar to flip-flops 258 and 260 will be needed for control of the analog-to-digital conversion of the pressure signal.

It can also be verified by inspection of FIG. 7 that, at the end of the inspiration phase immediately following initiation of the control circuitry, a logical "one" signal is generated on line 270 from the output of flip-flop 242. This is connected to the base of a transistor 272, the collector of which is connected through a resistor 274 to the gate terminal of a field effect transistor 276, the latter forming the logical switch 220 (FIG. 4). The effect of the logical "one" applied to the base of the transistor 272 is to lower the collector voltage output, which, in turn, renders the field effect transistor 276 non-conductive, thus substituting the voltage divider 230 for the operator-selected voltage divider 212 (FIG. 4) used to control the plateau time.

The control circuitry illustrated in FIG. 7 also includes a clock pulse generating circuit 278, for supplying clock pulses over line 280 to the analog-to-digital converters 26 (FIG. 1).

It can be seen from the foregoing that the present invention represents a significant advance in the respiration field. In particular the invention provides a novel method and means for determining and displaying patient compliance and resistance during the administration of intermittent positive pressure breathing therapy. It will be appreciated that, although a specific embodiment of the invention has been illustrated and described in detail for purposes of illustration, various modifications may be made without departing from the spirit and scope of the invention. Accordingly, the invention is not to be limited except as by the appended claims.

We claim:

1. For use with a respirator system of the volume-compensated type in which a preselected volume of gas is delivered to a patient during an inspiration phase of the patient breathing cycle, apparatus for the determination of patient compliance and resistance comprising:
    control means operable to initiate computation and display of patient compliance and resistance;
    means for sampling the system pressure at the end of the inspiration phase;
    means included within said control means for ensuring a plateau phase, following the inspiration phase and preceeding an expiration phase, long enough to allow the system pressure to equalize with the patient lung pressure;
    means for sampling the system pressure at the end of the plateau phase, to obtain a measure of the lung presure at the end of the inspiration phase;
    means for monitoring the actual volume of gas delivered to the patient; and
    means for computing and displaying patient compliance, as derived from the monitored volume and the system pressure sampled at the end of the inspiration phase, and patient resistance, as derived from the monitored volume and the two sampled values of the system pressure.

2. Apparatus as set forth in claim 1, wherein:
    said means for computing and displaying includes digital display means and analog-to-digital converter means; and
    said control means includes means for initiating operation of said analog-to-digital converter means.

3. Apparatus as set forth in claim 1, wherein said control means is able to be actuated both manually on demand and automatically on a periodic basis, to initiate operation of said apparatus.

4. Apparatus as set forth in claim 3, wherein said control means includes:
    switching means to change the value of a circuit parameter temporarily and thereby to substitute a relatively long plateau phase for one normally in effect; and
    switch control means for controlling operation of said switching means, and including manual means for enabling said switch control means on demand, and automatic means for enabling said switch control means automatically and periodically.

5. A method for the determination of the compliance and resistance of a patient undergoing breathing therapy from a respirator system for the delivery of a preselected volume of gas to the patient during an inspiration phase of each breathing cycle, said method comprising the steps of:
    monitoring respirator system pressure during each breathing cycle, the breathing cycle including the inspiration phase, a plateau phase during which exhalation is prevented, and an expiration phase;
    sampling the system pressure at the end of the inspiration phase and at the end of the plateau phase, whereby the sampled system pressure at the end of the plateau phase is substantially equal to the patient lung pressure at the end of the inspiration phase;
    measuring a compensated volume of gas delivered to the patient during the inspiration phase;
    diffenertiating the compensated volume with respect to time; and
    computing the patient compliance and resistance from the measured compensated volume, its time differential and the sampled system pressure values.

6. A method as set forth in claim 5, and further including displaying the computed values in a digital display device.

7. A method as set forth in claim 5, and further including the step of substituting for an operator-selected plateau phase a plateau phase of sufficient length to ensure equalization of system and lung pressures by the end of the plateau phase.

8. A method as set forth in claim 7, and further including the steps of:
    converting the computed compliance and resistance values to digital form;
    displaying the converted values in a digital display device; and
    initiating said steps of substituting, converting and displaying in response to an operator command and to a periodically generated starting signal.

9. A method as set forth in claim 8, wherein said steps of converting and displaying also include converting and displaying the lung pressure value.

10. Apparatus for use with a respirator system of the volume-compensated type in which a preselected volume of gas is delivered to a patient in each breathing cycle, the cylce having an inspiration phase, followed by a plateau phase during which exhalation is prevented, and an expiration phase, said apparatus being for the determination of patient compliance and resistance, and comprising:
    first electrical means for computing a respirator system pressure and a patient lung pressure both at the end of the inspiration phase of the breathing cycle, said first electrical means including means for ensuring a plateau phase long enough to allow the system and lung pressures to equalize, and means for sampling system pressure at the end of the inspiration phase and at the end of the plateau phase, whereby the system pressure at the end of the plateau phase is substantially equal to the lung pressure at the end of the inspiration phase;

means for obtaining a measure of compensated volume of gas delivered to the patient during the inspiration phase; and second electrical means for computing patient compliance from the compensated volume and the system pressure at the end of the inspiration phase, and for computing the patient resistance from the compensated volume and the system and lung pressures at the end of the inspiration phase.

11. Apparatus as set forth in claim 10, wherein said second electrical means includes:

differentiator means connected to generate a time differential of the compensated volume;

means for computing compliance by dividing the compensated volume by the lung pressure at the end of the inspiration phase; and means for computing resistance by dividing the difference between the system and lung pressures by the time differential of the compensated volume, all measured at the end of the inspiration phase.

12. Apparatus as set forth in claim 11, wherein said second electrical means further includes means for displaying the computed values of patient compliance and resistance.

13. Apparatus as set forth in claim 12, wherein:

said first and second electrical means operate on electrical analog signals representing the various quantities of pressure and volume;

said second electrical means further include analog-to-digital conversion means for converting the computed values of compliance and resistance into digital form; and said means for displaying the computed values of compliance and resistance is a digital display means.

* * * * *